United States Patent [19]

Pevsner

[11] Patent Number: 4,509,523

[45] Date of Patent: Apr. 9, 1985

[54] METHOD OF USING MINIATURE BALLOON CATHETER FOR PERFUSING

[76] Inventor: Paul H. Pevsner, 4121 Kingcrest Pkwy., Richmond, Va. 23221

[21] Appl. No.: 430,217

[22] Filed: Sep. 30, 1982

Related U.S. Application Data

[63] Continuation-in-part of Ser. No. 286,100, Jul. 22, 1981.

[51] Int. Cl.³ ............................................. A61M 25/00
[52] U.S. Cl. .................................... 128/658; 128/325; 604/53; 604/96
[58] Field of Search ............... 128/325, 344, 656–658; 604/96–103, 51–53

[56] References Cited

U.S. PATENT DOCUMENTS

| | | | |
|---|---|---|---|
| 3,292,627 | 12/1966 | Harautuneian | 604/100 |
| 4,029,104 | 6/1977 | Kerber | 128/656 X |
| 4,085,757 | 4/1978 | Pevsner | 128/344 X |
| 4,254,774 | 3/1981 | Boretos | 128/344 X |

*Primary Examiner*—Dalton L. Truluck
*Attorney, Agent, or Firm*—Griffin, Branigan & Butler

[57] ABSTRACT

This method of using a miniature balloon (102) in blood vessels (104) usually involves using a balloon that is thinner, more delicate (with thickness-controlled walls) than most balloons made previously. The process includes the steps of inserting the balloon (102) into a blood vessel (104) on the end of a cannula (106), inflating the balloon through the cannula until the balloon bursts, and then perfusing perfusate into the blood vessel via the burst balloon (108).

6 Claims, 9 Drawing Figures

METHOD OF USING MINIATURE BALLOON CATHETER FOR PERFUSING

BACKGROUND OF THE INVENTION

This application is a continuation-in-part of application Ser. No. 286,100 filed July 22, 1981.

This invention relates generally to the art of miniature balloon catheters for use in blood vessels, and more particularly, to miniature blood vessel balloon catheters of a type described in U.S. Pat. Nos. 4,085,757 and 4,213,461 (and related applications), to Pevsner and 4,029,104 to Kerber. In this respect, the information contained in those patents is incorporated herein by reference.

Balloon catheters of the type used in this invention are extremely small, since they must fit into very small blood vessels. In this regard, these balloons have diameters in the range of 0.018–0.033 inch, and are designed to be introduced into a body through 5 French, or less introduction catheters.

There are presently, at least two types of miniature blood-vessel balloon catheters with which this invention is concerned, namely detachable and perfusion. A detachable balloon 12 is depicted in FIG. 1 in a blood vessel 10. Basically, the detachable, or pop-off, balloon 12 is attached to an elongated, flexible, cannula (sometimes called catheter) 14 at a metallic, hollow, pin 16, which is affixed to the end of the cannula 14. The balloon 12, is contracted onto the pin 16 at an enlarged, plug-material, portion 18 having a surrounding compression band 20.

Briefly, in operation, the balloon 12 is introduced through a 5 French catheter into a blood vessel using a delivery device, such as the device disclosed in U.S. Pat. No. 4,159,022 to Paul H. Pevsner. Using this delivery device, the balloon is manipulated to pass through blood vessels, making turns when necessary, and going into branches where desired, by means of "parachute effect", and various other manipulations. To accomplish this, a surgeon, among other things, inflates and deflates the distal inflatable portion 22 of the balloon 12 via the flexible cannula 14 (whose proximal end is outside of the body) and the metallic, hollow, pin 12. When the inflatable portion 22 is inflated it is driven by blood flow with a "parachute effect." In this respect, the surgeon must continually inflate and deflate the inflatable portion 22 according to exigencies of the tortuous path he is trying to get the balloon to follow. Once the balloon arrives at its desired destination, a procedure that is performed with the balloon is to inflate the inflatable portion 22 until its outer surface contacts the inner surface of the vessel 10, as is shown by dashed lines in FIG. 1. The balloon is then further inflated to provide pressure releasing the metallic pin 16 from the plug-material portion 18 and the cannula 14 from a shroud portion 24 of the balloon. In addition, in some embodiments there is a hole 26 in the side of the metallic pin 16 which, when pressure within the hollow pin 16 becomes great enough, begins to significantly expand the shroud 24, thereby aiding in release of the cannula 14 and the pin 16 by the shroud 24 and the plug-material portion 18. Once the cannula 24 and the pin 16 are withdrawn from the balloon 12, the plug material 14, in conjunction with a compression band 20, seals the mouth of the inflatable portion 22, thereby leaving the inflatable portion 22 inflated as is shown in dashed lines 22' in FIG. 1. Thus, the inflated balloon is left wedged within the blood vessel 10, with the walls of the blood vessel 10 bulging out somewhat at the balloon, as is indicated by dashed lines at 10'.

A perfusion balloon system of FIG. 2 operates substantially the same as the device of FIG. 1 with regard to the method of transporting the balloon to a position within a blood vessel 10. However, once a perfusion balloon 28 is in a desired position, it is not "popped off" as is the balloon 12 of FIG. 1. Instead, in the prior art, an inflatable portion 30 has a reinforced hole 32 in the tip thereof which is substantially closed when the balloon is uninflated or inflated to only a small degree. However, when the balloon is significantly inflated, as is shown by dashed lines 34 in FIG. 2, the perfusion hole 32 opens up and a perfusion liquid is perfused into the blood vessel 10. Thereafter, the balloon is deflated and pulled out of the body, along with the cannula 14 and a metallic pin 36. It should be noted that the metallic pin 36 is different from the metallic pin 16 in that it does not include a hole 26. Further, the balloon system of FIG. 2 differs from the balloon system of FIG. 1 in that the pin 36 is more solidly attached to the balloon 28, so that the balloon 28 does not detach, or pop-off, as does the balloon 12 of FIG. 1.

Although the prior-art method of perfusing is highly beneficial for many applications, this invention provides another method of perfusing into a blood vessel with a miniature balloon which is superior for other applications.

It will be appreciated by those skilled in the art that the balloons 12 and 28 of FIGS. 1 and 2, respectively, must have inflatable portions 22 and 30 which easily inflate and deflate when desired for aiding in the delivery of the balloons to desired locations, while not prematurely beginning the procedures of the respective balloon systems, namely, detaching the balloon of FIG. 1, or perfusing from the balloon of FIG. 2. Further, the inflatable portions 22 and 30, when fully inflated to pop off or perfuse, must not rupture blood vessel walls 10 in order to perform these procedures. In other words, the pressure forces must be carefully balanced so that the balloons inflate and deflate for transportation, inflate completely for performing their main procedures, and perform their main procedures without rupturing blood vessels.

In this regard, when perfusing through the referenced hole 32 of FIG. 2 one must be careful not to try to perfuse too fast and thereby risk inflating the balloon to such an extent that it ruptures the blood vessel. When perfusing with such a method the speed at which one can perfuse through a small hole depends not only on the construction of the balloon but also on the thickness of the perfusate. Thus, it is an object of this invention to provide a method of perfusing with a miniature balloon which allows one to perfuse faster than previously but in which the danger of rupturing blood vessels is not so great as it was previously. However, it is also an object of this invention to provide such a new method of perfusing which still allows the use of a balloon which can be "parachuted" into position in the same manner as previous balloons described above.

In the past, such balloons have been constructed by dipping mandrils which are shaped like the balloons into a container, or vat, of liquid silicone rubber (silicone rubber dissolved in a solvent such as ethyl ether, Trichlorethylene, phenol or butyl alcohol). The liquid silicone rubber adheres to the mandril, and when the mandril is removed from the vat the silicone rubber cures, or dries. Thereafter, the balloon is removed from the mandril. Such a silicone rubber solution (liquid silicone rubber) has been formed of approximately 15% silicone rubber and 85% solvent. Normally the mandril need only be dipped into the solution once. Such a prior art system of making balloon catheters is fully described in U.S. Pat. No. 4,213,461 to Paul H. Pevsner.

A problem with balloons constructed by dipping a mandril into a vat of silicone rubber solution is that the walls of the balloon are relatively thick, thereby making the balloons too large to go into many smaller vessels and also requiring excessive pressure to inflate the balloons to perform desired functions therewith. That is, the balloons rupture walls of smaller vessels prior to performing their functions. Another difficulty with unduly thick walls is that the balloons cannot navigate tortuous turns in small vessels of the head, pelvis and bowels.

This application describes a method of making balloons for miniature balloon catheters which have thinner, and more delicate, walls than the walls of prior-art balloon catheters. By using this new method the thickness of balloon walls can be controlled to a greater degree than was previously possible.

SUMMARY

According to principles of this invention balloon catheters constructed to have thin, thickness-controlled, walls are "parachuted" into position in blood vessels. Thereafter, the balloons are inflated via an attached cannula until they burst. A perfusate is then inserted via the cannula into the blood vessel through the burst balloon.

BRIEF DESCRIPTION OF THE DRAWINGS

The foregoing and other objects, features and advantages will be apparent from the following more particular description of a preferred embodiment of the invention, as illustrated in the accompanying drawings in which reference characters refer to the same parts throughout the different views. The drawings are not necessarily to scale, emphasis being placed upon illustrating principles of the invention in a particular manner.

DESCRIPTION OF THE PREFERRED EMBODIMENT

Figure 1:
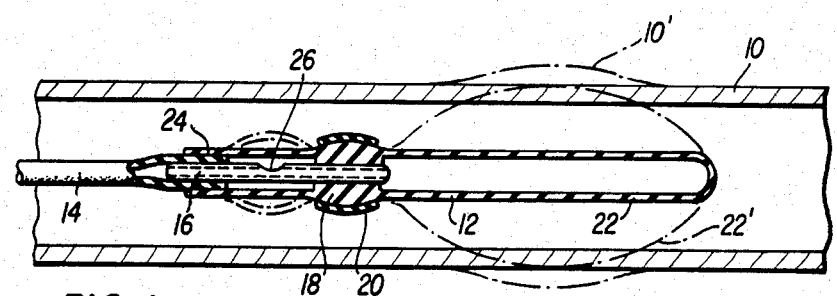
FIGS. 1 and 2 are side-sectional views depicting prior-art balloon catheters of a type with which this invention is concerned, mounted on cannulas and pins in blood vessels, FIG. 1 depicting a pop-off balloon, and FIG. 2 depicting a perfusion balloon.
Figure 2:
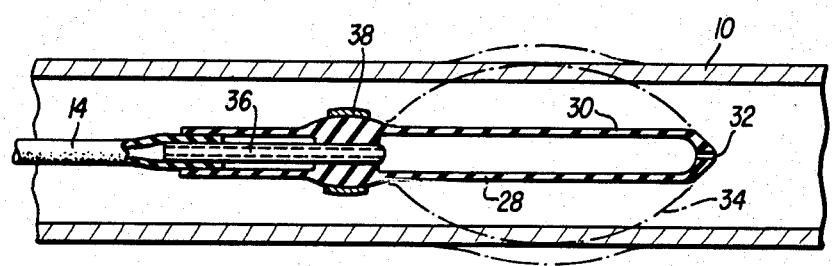
Figure 3:
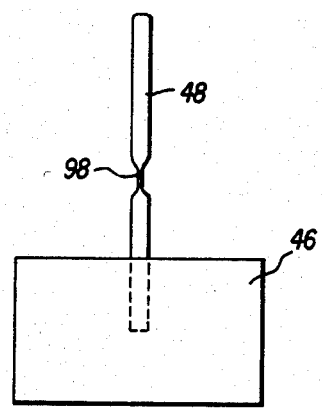
FIG. 3 is a side view of a mandril for making a pop-off balloon according to principles employed in making a perfusion balloon used in the method of this invention.
Figure 4:
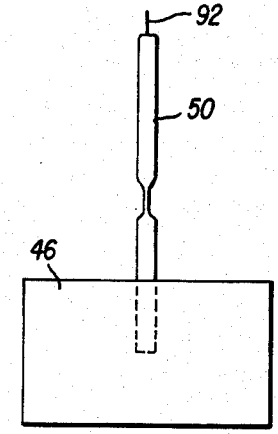
FIG. 4 is a side view of a mandril for making a perfusion balloon used in the method of this invention.
Figure 6:
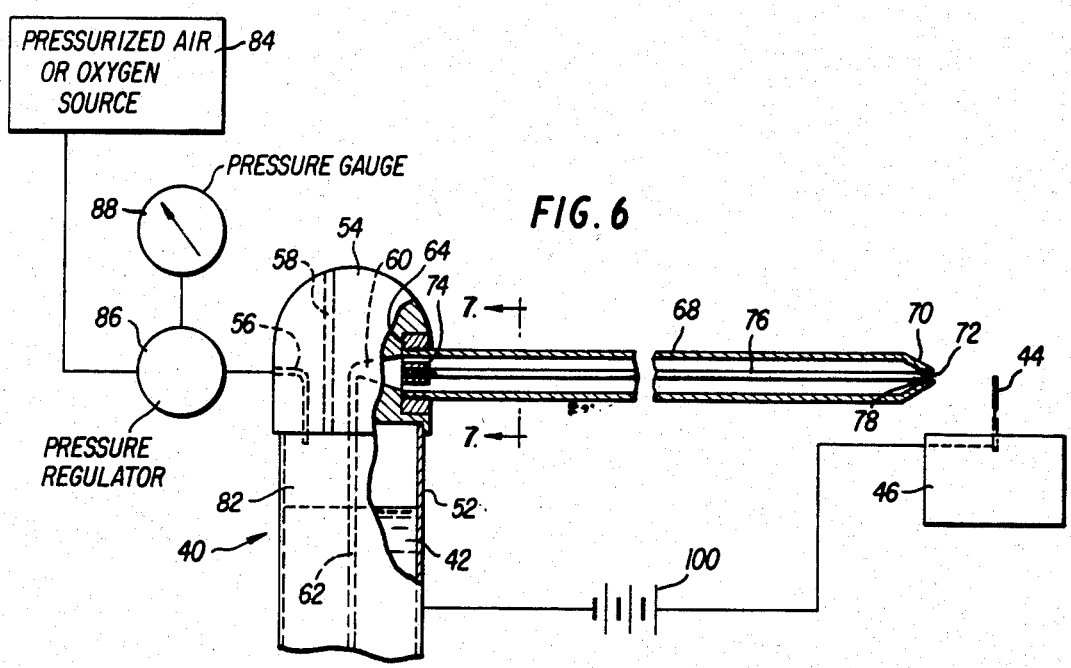
FIG. 6 is a side view, shown partially in section and partially in schematic, of spraying apparatus for making balloons used in the method of this invention.
Figure 7:
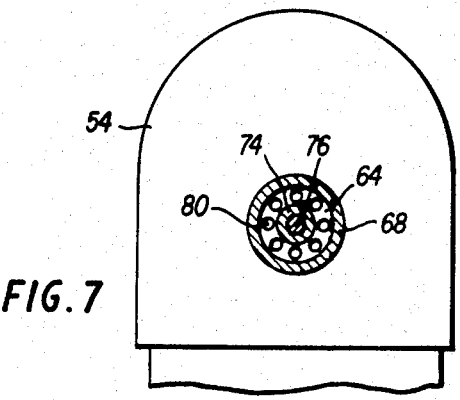
FIG. 7 is a view taken on lines 7—7 of FIG. 6.

Referring to FIG. 6, an aerosol sprayer 40 is being used to spray liquified silicone (a silicone solution comprising approximately 5% silicone rubber and 95% solvent) 42 onto a mandril 44 which is mounted on a cork block 46. With regard to the mandril 44, and the block 46, enlarged views thereof are depicted in FIGS. 3 and 4, with FIG. 3 depicting a mandril 48 for making pop-off type balloons of FIG. 1 and FIG. 4 depicting a mandril 50 for making perfusion balloons of FIG. 2.

The aerosol sprayer 40 includes a container 52 and a removable top 54 which can be removed for filling the container 52 with silicone solution 42. The removable top 54 includes an air-inlet passage 56, an exhaust passage 58, and an outlet passage 60. The outlet passage 60 communicates with a dip tube 62, which extends downwardly into the silicone solution 42. The container 52 and the removable top 54 are about 2 inches tall. The shell of such an aerosol sprayer is described and sold in the American V. Mueller Catalog, No. 80, Page 739, and is identified therein as Devilbiss Syringe 177. However, the Devilbiss Syringe 177 used for this invention is modified in that a plate 64 is soldered at the mouth of its outlet passage 60. The plate 64 includes female threads 66 into which male threads of an aluminum, one centimeter, outer-diameter, tube 68 is screwed. It should be noted that the outer end 70 of the tube 68 is beveled inwardly culminating at a hole 72 which is 1.5 mm across when fully opened. The plate 64 also has mounted thereon a female-threaded socket 74 into which a 2-2.5 mm needle 76 is screwed. The needle 76 has a tip 78 which is beveled at approximately a 30° angle, approximately the same as the bevel of outer end 70 of the tube 68, and is positioned to be in the opening 72 of the tube 68. The pointed tip 78, in combination with the hole 72 causes pressurized fluid to be aerosolized when it is forced through the hole 72. Axial adjustment of the pin 76 relative to the hole 72 is made by removing the tube 68 from the female threads 66, and rotating the needle 76 to cause movement due to threads 74. Thereafter, the tube 68 is again screwed into the threads 66. From FIG. 6 it can be seen that the plate 64 has numerous holes 80 therein to allow silicone solution 42 flowing through the dip tube 62 and the outlet passage 60 to pass into the tube 68 around the needle 76.

The container 52 is pressurized in a space 82 above the silicone solution 42 through the air-inlet passage 56 which communicates with a pressurized air, or oxygen, source 84 via a pressure regulator 86. A pressure gauge 88 enables an operator to know what pressure is being applied to the space 82. With regard to this pressure, pressure sources are available in hospitals ranging from 100–1,000 psi, however, the pressure applied to the space 82 in the aerosol sprayer 40 should be less than 25 psi. Thus, the pressure regulator 86 must be sized in accordance with the pressurized air source 84.

Once pressurized air, or oxygen, is being applied through the air-inlet passage 56, the space 82 will be pressurized if the exhaust passage 58 is covered, however, it will not be significantly pressurized if the exhaust passage 58 is not covered. Thus, the exhaust passage 58 acts as an on/off switch which can be actuated by an operator covering it, or not covering it, with his finger.

In making perfusion balloons used in the method of this invention, as well as in making other beneficial balloons, one mixes a silicone solution 42 having a concentration of silicone to solvent 42 of less than 15%, preferably around 5%, and puts this in the aerosol sprayer 40 by removing the container 52 from the removable top 54. Once the container 52 is again screwed onto the removable top 54, pressure from the pressurized air source 84 is applied through the pressure regulator 86 to the space 82 via the air-inlet passage 56, this pressure being something less than 25 psi, preferably between 15 and 25 psi. The operator adjusts the relative positions of the tube 68 and the needle valve 76, testing the mechanism by placing his finger over the exhaust passage 58. If liquid silicone is not aerosolized when it is ejected from the hole 72, the operator must remove his finger from the exhaust passage 58 and readjust the relative positions of the tube 68 and the needle valve 76. This procedure is repeated until operation of the device aerosolizes the silicone solution.

Figure 5:
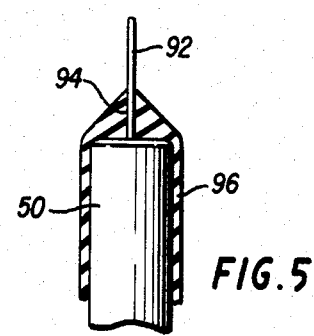
FIG. 5 is a close-up side view, shown partially in section, of the tip of the mandril of FIG. 4 having silicone rubber coated thereon.

Now the operator aims the aerosolized silicone solution at the mandril 44, which is stationarily mounted on a cork block 46, to thereby apply the aerosolized silicone solution to the mandril, manipulating the aerosol sprayer 40 about the mandril 44. The operator can cause a buildup 90 of silicone solution at various points on the mandril as he desires. For example, with reference to FIG. 5, the operator can cause a buildup 90 of silicone about a needle 92 which molds a perfusion hole 94 in a balloon 96 being made. This buildup 90 reinforces the perfusion hole 94, which is desirable as is fully described in U.S. Pat. No. 4,213,461 to Paul H. Pevsner. Similarly, a buildup can be caused at an indentation 98 (FIG. 3) in the mandril 48 to create plug material corresponding to the plug material 18 of FIG. 1.

So much solution is thusly applied to the mandril 44 to create a thin, approximately-uniform, coat of silicone solution, with the exception of those areas where the operator has tried to create a buildup. The coat can be virtually as thin as the operator desires, and certainly should not be sufficiently thick to cause "runs" of drops down the mandril. If the operator desires to have a thicker (although thinner than most dipped balloons) balloon, he allows the first coat of silicone solution to cure (air cure from 24–48 hours, oven cure at 130°–140° F. for around ½ hour), and then he applies a second coat. An average balloon requires approximately three coats of silicone solution and even so this composite coat is thinner and more delicate than a normal coat which is created by dipping a mandril in silicone solution once. An operator can control balloon wall thickness by controlling the number of coats.

An embellishment of this method is to apply a positive terminal of an electrical source 100 to the mandril 44 and its negative terminal to the aerosol sprayer 40. Thus, aerosol mist particles have negative charges which are attracted to the positive charge of the mandril. In this respect, it has been learned that even if the aerosol sprayer, and the particles emitted therefrom, are not energized by an electrical source, the mist particles are normally negatively charged. Therefore, it is really only necessary to positively charge, or ground, the mandril 44 in order to get attraction. However, for completeness sake, an electrical source 100 is shown in FIG. 6 which may be necessary under different conditions than those which existed for tests which have been run to date. It should be noted that this invention works quite well even without employing an electrical source.

It has been found from tests that minute particles of metal, such as titanium, barium, tantalum, bismuth, and silver can be mixed in the silicone solution 42 and sprayed with the aerosol sprayer 40. Such particles, are also aerosolized and are uniformly spread on the mandril 44. When thusly used, the container 52 is shaken to keep the minute metallic particles uniformly distributed within the silicone solution 42 prior to spraying.

Yet a further embellishment of this method is to cover the mandrils 44, 48 and 50 with a coat of Teflon and then to roughen this coat of Teflon with very fine sandpaper, or the like. The purpose of the "roughening" is to make it easier for the aerosolized particles to adhere to the mandril. This could be accomplished simply by roughening the surface of a metal mandril 44, however, when this is done it is somewhat difficult to remove the balloon from the mandril. Thus, Teflon is applied, and the Teflon is roughened. With regard to removing balloons from the mandril, this can be accomplished by dilating the balloons with a solvent, such as ethyl ether.

It will be understood by those skilled in the art that the method produces thinner and more delicate miniature balloon catheters than did the prior-art "dipping" method. In addition, this method allows one to make uniform, radio-opaque miniature balloon catheters which are superior to those which could be made in the prior art.

When balloons are made with this method, they can be made sufficiently thin that the balloons can be inflated and exploded before the walls of the balloon even contact the walls of blood vessels, which thereby allows one to use the inflation/deflation aspect of the balloon to help transport it to a proper position using "parachute effect" and thereafter enables the operator to explode the balloon by overinflating it, without risking damage to the vessel.

Figure 8:
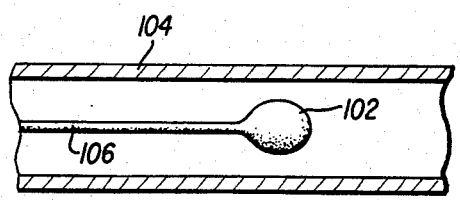
FIGS. 8 and 9 are side cutaway views of a balloon catheter in a blood vessel being used to perform the method of this invention.
Figure 9:
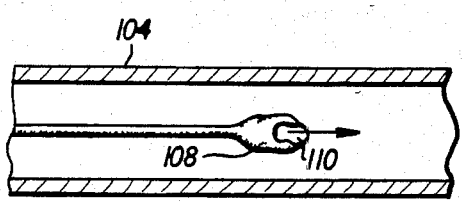

In this respect, the method of practicing this invention is depicted in FIGS. 8 and 9. In practicing the method of this invention, a perfusion balloon 102 having no perfusion hole therein, but being constructed to be extremely thin in accordance with the spraying method described above, is introduced into a blood vessel 104 and guided to an appropriate position within the blood vessel 104 by inflating and deflating the balloon 102 via a cannula 106. Once the balloon 102 is in an appropriate position, it is inflated further via cannula 106 until it bursts. In the preferred embodiment, the balloon is designed to lightly touch the walls of the blood vessel 104 before it bursts in order to provide a greater margin for inflating and deflating the balloon 102 during positioning, however, in some embodiments, the balloon is designed to burst before it wedges itself in the blood vessel 104 in order to provide a greater safety margin for protecting the blood vessel against being ruptured. In any event, once the balloon 102 has burst it becomes a deflated balloon 108 having a rather large rupture hole, or holes, 110 therein. At this point, a perfusate is introduced into the cannula 106 from outside the body and this perfusate is forced through the cannula 106 and the balloon 108 into the blood vessel 104 via the rupture hole, or holes, 110.

Still further, balloons can be made sufficiently thin and delicate with the method described herein so that the releasability at desired pressures can be chosen to a finer degree, not previously possible under a prior-art "dipping" technique for making balloons.

Balloons made with the method described herein have been introduced easily through 4 French catheters, which was not practical with dipped balloons. Further, balloons made with this method have been transported into smaller vessels than was previously possible with dipped balloons. In addition, it is noted that about six sprayed coats according to the method of this invention is equal to one dipped coat according to the prior art. However, even where a sufficient number of coats is sprayed onto a mandril to create a balloon of the thickness of a dipped balloon, the sprayed balloon is superior in that it is more flexible. This phenomenon is not understood by the inventor. It is noted that prior-art dipping is done in a 15% solution because when the solution is thinner an insufficient amount sticks to the mandril.

While the invention has been particularly shown and described with reference to preferred embodiments, it will be understood by those skilled in the art that various changes in form and detail may be made therein without departing from the spirit and scope of the invention.

It is noted that much of the apparatus described herein is of a research nature because applicant has not progressed beyond this point in the development of this invention.

The embodiments of the invention in which an exclusive property or privilege are claimed are defined as follows:

1. A diagnostic and therapeutic method for carrying out perfusion procedures in small vessels comprising the steps of:
    preparing a miniature balloon catheter assembly including an inflatable balloon formed to be extremely thin by aerosolizing balloon-catheter-material solution onto a mandril and allowing it to cure, said balloon having no perfusion hole therein and being connected to a distal end of a resilient cannula, said balloon and said cannula having a size for insertion into blood vessels and said inflatable balloon being constructed to be inflated and deflated in said blood vessels for being transported and directed therein by the flow of blood, said balloon being further constructed to be inflated until bursting in a particular blood vessel without damaging said particular blood vessel;
    inserting the distal end of said cannula including said inflatable balloon, into a blood vessel;
    attaching the proximal end of said cannula to a source of pressurized fluid and pressurizing the balloon to partially inflate the balloon to permit the balloon and the attached cannula to be transported by blood flow within the vessel to said particular blood vessel;
    increasing the fluid pressure inside the balloon portion to expand the thin balloon portion until said balloon portion bursts, thereby causing a rupture hole in the thin balloon; and
    inserting a therapeutic perfusate into the proximal end of said cannula and perfusing said perfusate into said blood vessel via said ruptured hole in said burst balloon.

2. A method as in claim 1 wherein said balloon is made by the steps of: aerosolizing a first coat of said balloon-catheter material solution onto said mandril; allowing said first coat to cure; thereafter aerosolizing at least one additional coat of said balloon-catheter material solution onto said cured coat; thereafter allowing said additional coat to cure, the number of coats being chosen to provide a particular bursting pressure; and then removing from said mandril said first cured coat and said additional cured coat as a unit forming said miniature balloon.

3. A method as in claims 1 or 2 wherein said balloon-catheter-material solution is a rubber solution mixed in proportions of less than 15 percent rubber to solvent.

4. A method as in claim 3 wherein said proportion of rubber is around 5 percent.

5. A method as in claim 3 wherein said rubber is silicone.

6. A method as in claim 1 wherein said balloon-catheter-material solution is sprayed with an aerosol apparatus through an opening whose effective area is controlled by a needle valve.

* * * * *